Aug. 29, 1967 E. S. BOERNER Plant Pat. 2,763
ROSE PLANT
Filed Dec. 20, 1965
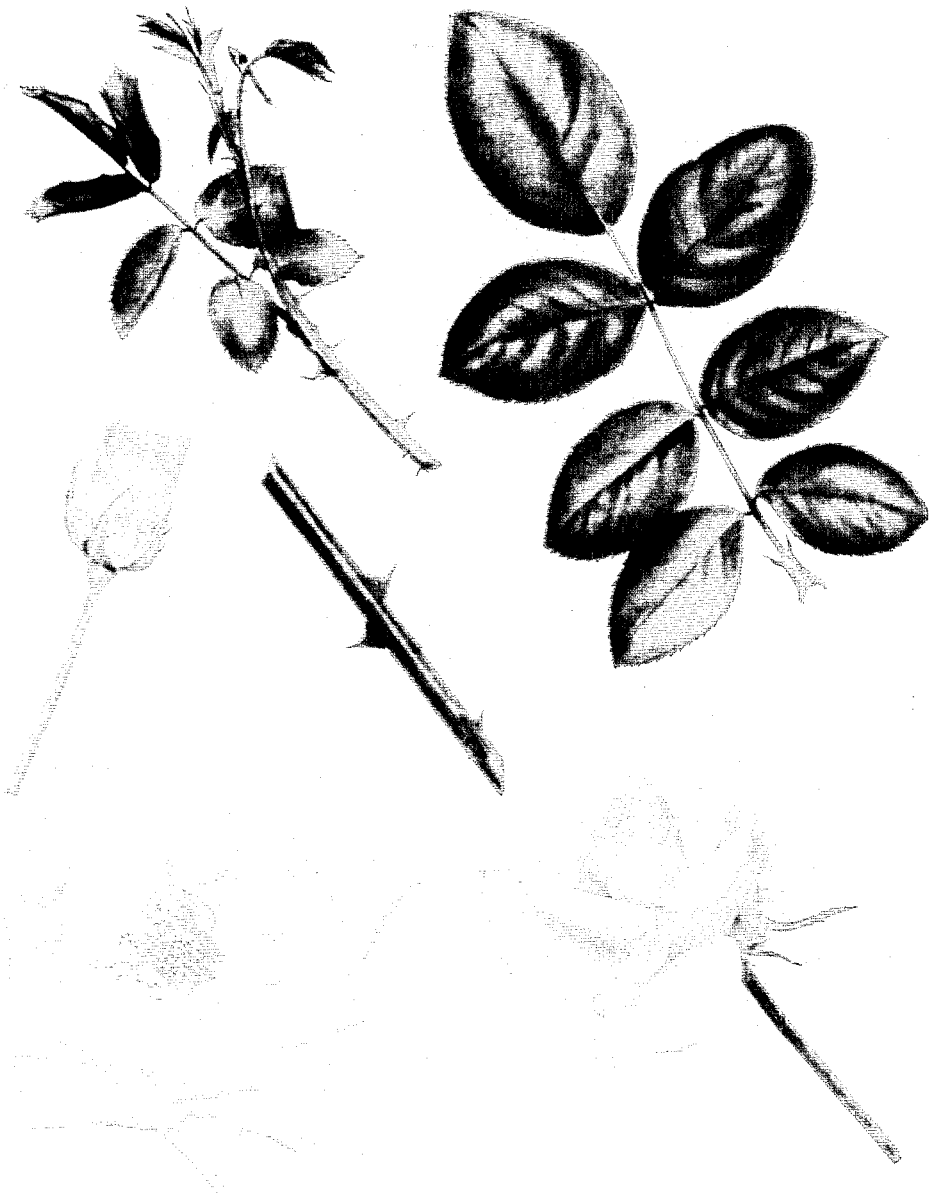
Inventor.
E. S. Boerner
By: Robb & Robb
Attorneys.

United States Patent Office

Plant Pat. 2,763
Patented Aug. 29, 1967

2,763
ROSE PLANT

Eugene S. Boerner, Newark, N.Y., assignor to Jackson & Perkins Company, Newark, N.Y., a corporation of New York

Filed Dec. 20, 1965, Ser. No. 514,154
1 Claim. (Cl. Plt.—26)

The present invention relates to a new and distinct variety of rose plant of the floribunda class, which was originated by me by crossing the variety "Spartan" (Plant Patent No. 1,357) with the variety known as "The Farmer's Wife" (Plant Patent No. 2,196).

The primary objective of this breeding was to produce a new and improved rose variety of the floribunda class which bears flowers similar to those of the parent variety "Spartan," but which are larger and lighter in color. This objective was fully achieved along with other desirable improvements, as evidenced by the following unique combination of characteristics which are outstanding in the new variety and which distinguish it from its parents, as well as from all other varities of which I am aware:

(1) Ample foliage which clothes the plant all the way down to the ground;

(2) A very great freedom of bloom;

(3) The production of floribunda-type flowers, said flowers being larger in size than those of the parent variety "Spartan" and being produced both singly and in clusters; and (4) A distinctive and attractive general color tonality of the flowers corresponding to Orange-Pink, overcast with Shrimp Pink.

A sexual reproduction of my new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Spartan."
- *Pollen parent.*—"The Farmer's Wife."

Classification:
- *Botanic.*—Floribunda.
- *Commercial.*—Floribunda.

*Flower*

(Observations made from specimens grown outdoors at Newark, N.Y., in the early morning during the first part of the month of August.)

Blooming habit: Recurrent—continuous.

But:
- *Size.*—Medium.
- *Form.*—Ovoid; is not affected by wet or hot weather.
- *Color.*—When sepals first divide—Strawberry Pink, Plate 1. When petals begin to unfurl—Geranium Pink, Plate 1, lightly overcast with Strawberry Pink, Plate 1, with lower half of petal overcast with Barium Yellow, Plate 16. When half-blown: inside of petals—Grenadine Pink, Plate 2, with lower half of petal overcast with Orient Pink, Plate 2, reverse of petals—Strawberry Pink, Plate, overcast with Safrano Pink, Plate 2.
- *Sepals.*—Slightly branched; curl back when petals begin to unfurl. Color: inside—Turtle Green, Plate 32, outside—light Elm Green, Plate 17.
- *Calyx.*—Color—Light Elm Green, Plate 17. Shape—funnel. Size—small. Aspect—smooth. Odor when rubbed—none.
- *Peduncle.* — Length — long. Aspect — Smooth. Strength—erect; slender. Color—Parrot Green, Plate 6.
- *Opening.*—Opens up well; is not affected by adverse weather conditions.

Bloom:
- *Size.*—Large. Average size when fully expanded—from 4½ inches to 5 inches.
- *Borne.*—Both singly and in clusters; very free.
- *Stems.*—Long; strong.
- *Form (when first open).*—From cupped to flat. Permanence—retains its form to the end.
- *Petalage.*—Double (full but open center). Number of petals under normal conditions—from 30 to 35.
- *Color.*—Center of flower—Orange-Pink, Plate 2, very lightly overcast with Eosine Pink, Plate 1. Outer petals—Seashell Pink, Plate 14, overcast with Shrimp Pink, Plate 1. Base of petals (aiglet)—Primrose Yellow, Plate 30. Inside of petals—Orange-Pink, Plate 2, overcast with Shrimp Pink, Plate 1. Reverse of petals—Shrimp Pink, Plate 1, overcast very lightly with Safrano Pink, Plate 2. General tonality from a distance—Orange-Pink, Plate 2, overcast with shrimp Pink, Plate 1.
- *Discoloration.*—General tonality at end of first day—Orange-Pink, Plate 2, overcast with Shrimp Pink, Plate 1. Second day—Orange-Pink, Plate 2, overcast with Shrimp Pink, Plate 1. Third day—Shrimp Pink, Plate 1.

Petals:
- *Texture.*—Thick; is not affected by wet or hot weather.
- *Appearance.*—Inside—satiny. Outside—shiny.
- *Form.*—Oval.
- *Arrangement.*—Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—very long. As cut flower—very long.

*Genital organs*

Stamens, anthers: Medium size; many; regularly arranged around styles. Color—Flesh-Ocher, Plate 14.
Stamens, filaments (threads): Medium length. Color—Light Ochraceous-Salmon, Plate 15.
Pollen: Color—Pale Salmon-Color, Plate 14.
Styles: Bunched; uneven length; short; thin.
Stigmas: Color—Alizarine Pink, Plate 13.
Ovaries: All enclosed in calyx.
Hips: None.
Seeds: None.

*Plant*

Form: Bush.
Growth: Vigorous; upright.
Foliage: Compound of 3 to 5 leaflets.
- *Size.*—Medium.
- *Quantity.*—Abundant; down to the ground.
- *Color.*—New foliage: Upper side—Oil Yellow, Plate 5, with outer edge of leaf overcast with Garnet Brown, Plate 1; under side—Van Dyke Red, Plate 13, with upper half of leaf overcast with Yellowish- Oil Green, Plate 5. Old foliage: upper side—Spinach Green, Plate 5; under side—Rainette Green, Plate 31.

*Shape.*—Oval pointed.

*Texture.*—Upper side — leathery. Under side — smooth.

*Ribs and veins.*—Ordinary.

*Edge.*—Serrated (saw toothed).

*Serration.*—Both double and single; small.

*Leaf stem.*—Color—Bice Green, Plate 17. Under side—smooth.

*Stipules.*—Medium length; smooth.

Wood:

*New wood.*—Color—Yellowish Oil Green, Plate 5. Bark—smooth.

*Old wood.*—Color—Cress green, Plate 31. Bark—smooth.

Thorns:

*Thorns.*—Quantity: on main stalks from base—ordinary; on laterals from stalk—ordinary. Form—narrow base; medium length; straight and hooked upward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of ample foliage which clothes the plant all the way down to the ground, a very great freedom of bloom, the production of floribunda-type flowers, said flowers being larger in size than those of the parent variety "Spartan" and being produced both singly and in clusters, and a distinctive and attractive general color tonality of the flowers corresponding to Orange-Pink, overcast with Shrimp Pink.

No references cited.

ABRAHAM G. STONE, *Primary Examiner.*

ROBERT E. BAGWILL, *Examiner.*